(12) United States Patent
Eryilmaz et al.

(10) Patent No.: US 11,485,948 B2
(45) Date of Patent: Nov. 1, 2022

(54) PROCESS FOR PROVIDING A CULTURE OF MICROORGANISMS TO AN ELONGATED ELEMENT

(71) Applicant: Sanko Tekstil Isletmeleri San. Ve Tic. A.S., Inegol-Bursa (TR)

(72) Inventors: Jitka Eryilmaz, Inegol-Bursa (TR); Ece Senel, Inegol-Bursa (TR); Seref Agzikara, Inegol-Bursa (TR); Nejdiye Gunes, Inegol-Bursa (TR); Fehim Caglar, Inegol-Bursa (TR); Semih Kazanc, Inegol-Bursa (TR); Ozgur Cobanoglu, Inegol-Bursa (TR)

(73) Assignee: Sanko Tekstil Isletmeleri San. Ve Tic. A.S., Inegol-Bursa (TR)

( * ) Notice: Subject to any disclaimer, the term of this patent is extended or adjusted under 35 U.S.C. 154(b) by 0 days.

(21) Appl. No.: 16/436,046

(22) Filed: Jun. 10, 2019

(65) Prior Publication Data

US 2019/0376017 A1    Dec. 12, 2019

(51) Int. Cl.
| | |
|---|---|
| *C12M 1/26* | (2006.01) |
| *C12N 1/20* | (2006.01) |
| *C12M 1/12* | (2006.01) |
| *C12P 19/02* | (2006.01) |
| *C12P 3/00* | (2006.01) |
| *C12M 1/36* | (2006.01) |

(Continued)

(52) U.S. Cl.
CPC ............ *C12M 33/04* (2013.01); *C12M 23/06* (2013.01); *C12M 41/14* (2013.01); *C12M 41/36* (2013.01); *C12M 41/48* (2013.01); *C12N 1/00* (2013.01); *C12N 1/12* (2013.01); *C12N 1/14* (2013.01); *C12N 1/16* (2013.01); *C12N 1/20* (2013.01); *C12P 3/00* (2013.01); *C12P 19/04* (2013.01); *D06M 16/003* (2013.01); *C12N 2527/00* (2013.01); *C12N 2533/00* (2013.01); *C12R 2001/00* (2021.05)

(58) Field of Classification Search
None
See application file for complete search history.

(56) References Cited

U.S. PATENT DOCUMENTS

2017/0314193 A1* 11/2017 Eryilmaz ............. D03D 13/004

FOREIGN PATENT DOCUMENTS

| | | |
|---|---|---|
| CN | 106010965 | 10/2016 |
| CN | 207 227 839 | 4/2018 |

(Continued)

OTHER PUBLICATIONS

International Search report and written opinion issued by the EPO dated Feb. 18, 2019 for PCT/EP2018/065506.

(Continued)

*Primary Examiner* — David W Berke-Schlessel
(74) *Attorney, Agent, or Firm* — Silvia Salvadori

(57) ABSTRACT

The present invention relates to a process for depositing at least a culture of microorganisms to an elongated element, preferably a yarn, comprising the steps of: providing at least a first feeding device comprising at least a first outlet; supplying at least one elongated element to said at least first feeding device; feeding to said first outlet at least a first culture comprising at least one microorganism; dispensing said first culture from said at least first outlet; contacting at least part of said elongated element with said first culture of microorganisms, to provide at least a part of said elongated element with an amount of said first culture of microorganisms.

25 Claims, 9 Drawing Sheets

(51) Int. Cl.
*D06M 16/00* (2006.01)
*C12P 19/04* (2006.01)
*C12M 1/00* (2006.01)
*C12N 1/00* (2006.01)
*C12M 1/34* (2006.01)
*C12N 1/12* (2006.01)
*C12N 1/14* (2006.01)
*C12N 1/16* (2006.01)
*C12R 1/00* (2006.01)

(56) References Cited

FOREIGN PATENT DOCUMENTS

JP             04141081 A    *   5/1992             C12M 33/20
JP             H04 141081       5/1992

OTHER PUBLICATIONS

European Search Report and written opinion issued by the EPO dated Jul. 16, 2019 for corresponding EP application No. 19179217.5.
Office Action issued by the EPO dated Mar. 21, 2022 for corresponding EP application No. 19179217.5.
Office Action issued by the EPO dated May 3, 2021 for corresponding EP application No. 19179217.5.
ETH Zurich: "30-printed living bacteria", Dec. 1, 2017 (Dec. 1, 2017), pp. 1-3, XP054981712, Retrieved from the Internet: URL:https://www.youtube.com/watch?v=W2piUVYukyA [retrieved on Apr. 24, 2021].

* cited by examiner

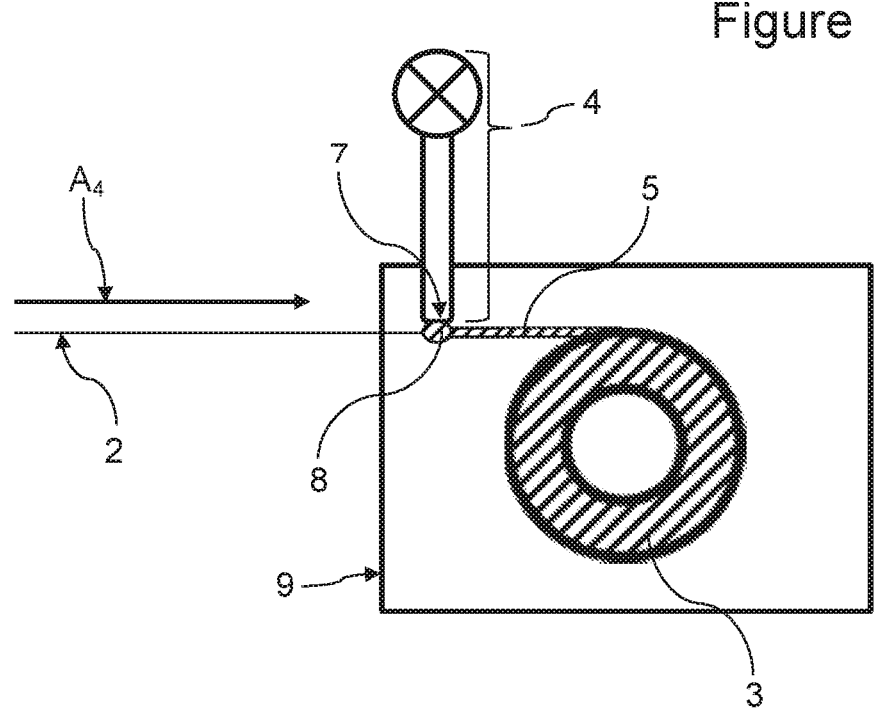

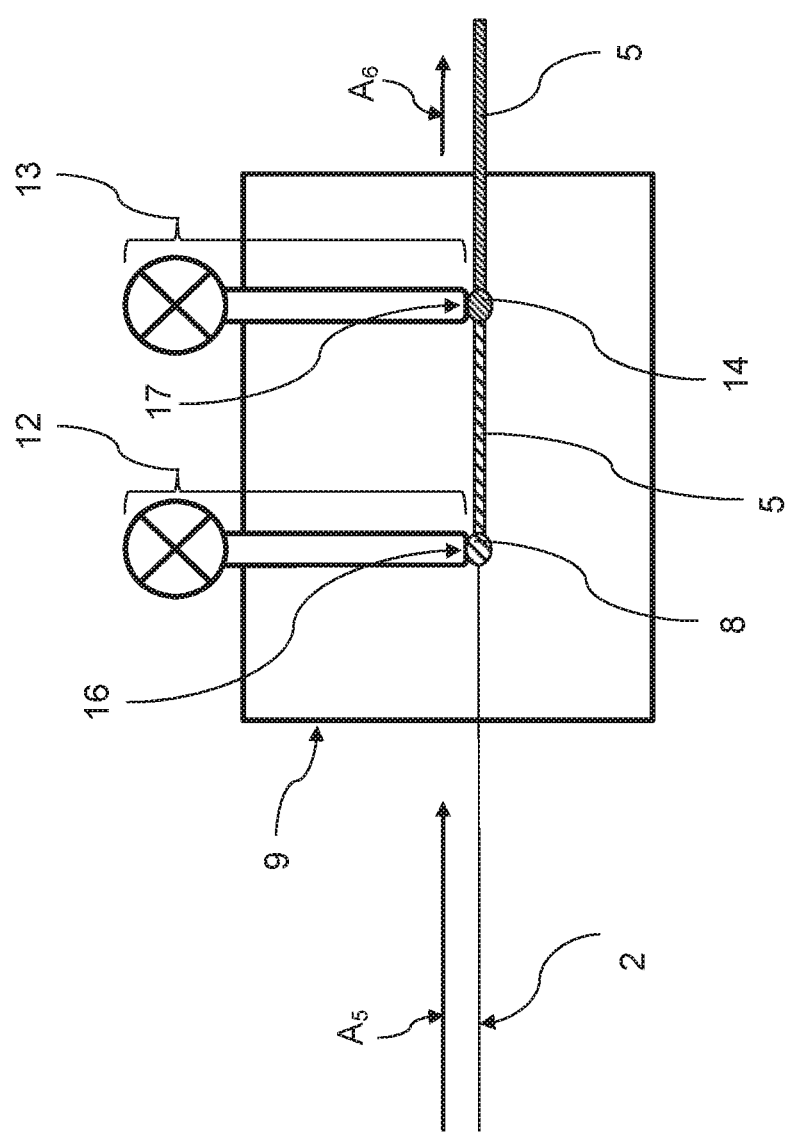

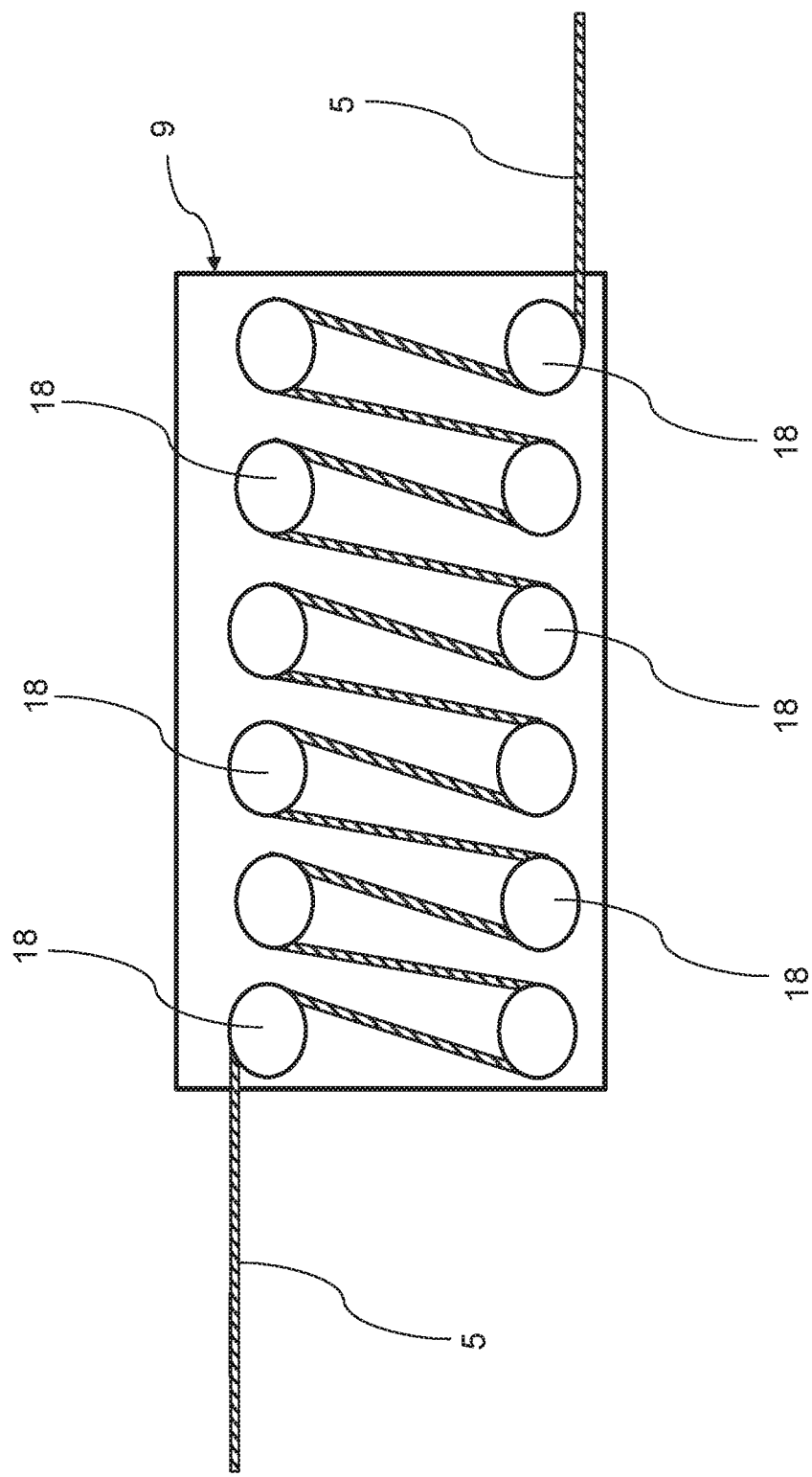

PROCESS FOR PROVIDING A CULTURE OF MICROORGANISMS TO AN ELONGATED ELEMENT

This application is a U.S. Non-Provisional application which claims priority to and the benefit of PCT Application No. PCT/EP2018/065506 filed Jun. 12, 2018, the content of which is incorporated herein by reference in its entirety.

FIELD OF THE INVENTION

The present invention relates to the textile field, in particular to the finishing of elongated elements, such as yarns. Specifically, the present invention relates to a process for providing a culture of microorganisms to elongated elements, preferably yarns.

BACKGROUND OF THE INVENTION

Many techniques and methods are available and known, to provide a textile article with a culture of microorganisms.

Methods are known wherein a textile article is dipped into a culture of microorganisms, i.e., is dipped into an impregnation bath comprising a culture of microorganisms. According to these methods, a textile article, such as a fabric, may be dipped into an impregnation bath comprising a culture of microorganisms, so that the textile article is impregnated with the culture of microorganisms.

For example, in U.S. Pat. No. 4,378,431 A, a method is disclosed for imparting hydrophilic characteristics to hydrophobic synthetic substrates, such as polyester fibers. In particular, a liquid culture medium inoculated with *Acetobacter* is placed into a shallow tray. Thereafter, a roll of polyester woven fabric is continuously fed so that the fabric is immersed into the culture medium for a period of time sufficient to allow attachment of the cellulose microfibrils. The fabric is then taken up on another roll and permitted to dry while the next successive portion is immersed in the medium.

However, the concentration of the microorganisms in the culture in the impregnation bath changes as the textile article, such as a fabric, is supplied to and dipped into the bath. Consequently, the culture of microorganisms is provided to the textile article in a non-homogeneous manner. In other words, different parts of the textile article are impregnated with different amounts of culture, so that further finishing treatments of the article may be jeopardized. Additionally, when the textile article is dipped into the bath, proteins, waxes and other impurities are released into the impregnation bath, thus changing the pH of the bath and of the culture of microorganisms, and changing the concentration of the microorganisms in the culture. Moreover, the impregnation bath requires a continuous monitoring/feeding/recovering system to maintain the stability of the culture media, i.e., to maintain the condition of the bath substantially unchanged during the dipping and impregnation of the textile article. In addition, the current impregnation baths are usually prone to contamination.

Other methods, based on spraying or spreading, are also available to provide a culture of microorganisms to a textile article.

US 2017/314193 A1 discloses a process for producing a fabric wherein a woven fabric is provided with a layer of at least one bacterial biopolymer on at least part of at least one side of said woven fabric to provide a composite fabric. US 2017/314193 A1 further discloses that, once a composite fabric is obtained, at least part of the fabric yarns are dyed together with the biopolymer layer. The layer of bacterial biopolymer is at least in part removed from the composite fabric to obtain a treated fabric. According to US 2017/314193 A1, the bacterial biopolymer layer can be grown directly on cotton yarns before the weaving by contacting yarns with a culture of bacterial biopolymer-producing microorganisms, and culturing said bacterial biopolymer-producing microorganisms, before the weaving, thus providing composite yarns. In particular, US 2017/314193 A1 discloses that the culture of bacterial biopolymer-producing microorganisms may be provided to the yarns by dipping the yarns into the culture of bacterial biopolymer-producing microorganisms or by spraying the culture of bacterial biopolymer-producing microorganisms on at least some of the yarns before weaving.

JP H04 141081 A discloses a continuous culture apparatus and a continuous method for culturing bacterial cells and recovering such bacterial cells from a carrier. In the continuous culture apparatus of JP H04 141081 A, a culture medium is supplied to a porous carrier from a medium supply unit. Cells are supplied to a porous separator from a cell supply unit. The porous carrier and the porous separator are brought into contact in a culture section while being circulated. In this culture unit, the medium contained in the porous carrier is supplied to the cells through the porous separating material, and the cells grow in gas phase. Bacterial cells grow on the porous separator, not on the porous carrier, and can be recovered only by and separating the porous separator from the porous carrier. According to JP H04 141081 A, the porous carrier may be formed by an endless belt-like nonwoven fabric, a woven fabric or the like, while the porous separating material may be in the form of a mesh, a porous film or the like.

However, spraying and spreading methods inflict severe disturbances to the biological content of the culture, in particular to microorganisms. For example, high pressure and viscosity levels are required for spray droplets formation, and micro-accelerations, such as in jet printing, are exerted upon microorganisms when these spreading methods are used. Therefore, currently available spraying methods and spreading methods are, in many cases, not suitable to provide a culture of microorganisms to a textile article.

SUMMARY OF THE INVENTION

It is an object of the present invention to solve the above mentioned problems and to provide a process for providing a culture comprising microorganisms to a textile, such as an elongated element, in a substantially homogeneous manner.

Another object of the present invention is to provide a process for providing a culture comprising microorganisms to a textile, such as an elongated element, wherein the characteristics of the culture and/or the culture media do not substantially change during the process.

A further object of the present invention is to provide a process for providing a culture comprising microorganisms to a textile, such as an elongated element, which allows for an accurate and substantially reproducible distribution of the culture onto the substrate.

A further object of the invention is to provide a process for providing a culture comprising microorganisms to a textile, such as an elongated element, wherein the contamination of the culture is effectively prevented.

These and other objects are illustrated in one or more of the appended claims.

The present invention relates to a process for depositing at least a culture of microorganisms to an elongated element, preferably a yarn, comprising the steps of:
- a) providing at least a first feeding device comprising at least a first outlet;
- b) supplying at least one elongated element, preferably a yarn, to said at least first feeding device;
- c) feeding to said first outlet at least a first culture comprising at least one microorganism;
- d) dispensing said first culture from said at least first outlet;
- e) contacting at least part of said elongated element with said first culture of microorganisms, to provide at least part of said elongated element with an amount of said first culture of microorganisms.

It has been surprisingly found that, through the process of the present invention, a culture comprising microorganisms can be provided to an elongated element, e.g., to a yarn, in a substantially homogeneous manner. In other words, substantially the same amount of culture may be provided to parts of the yarn having substantially the same length.

Also, advantageously, through the process of the present invention the characteristics and properties of the culture comprising microorganisms do not substantially change during the process. In particular, according to an aspect of the present invention, a predetermined amount of culture is dispensed from the first outlet to contact the elongated element (e.g., a yarn). An advantage of the present invention is thus that the culture comprising at least one microorganism is deposited onto the elongated element's surface, substantially avoiding the production of culture waste.

According to embodiments, the culture comprising microorganisms is confined into a feeding device having at least one first outlet, so that a predetermined amount of the culture is dispensed from the first outlet, whereas the remaining amount of the culture is substantially not released from the feeding device.

In this way, advantageously, possible contamination of the culture may be effectively prevented.

According to the present description, features of the present invention discussed with reference to the first outlet can be applied mutatis mutandis to further outlets, e.g., to a second outlet.

As used herein, the term "elongated element" refers to an element having a shape similar to a thread (i.e. a thread-like element). An example of elongated element is a yarn. In general, in an elongated element, two of the three dimensions are much lower than and generally negligible with respect to the third dimension. For example, an elongated element may have the shape of a strip having width and thickness negligible with respect to the length. Preferably, elongated elements have two of the three dimensions comparable between them and negligible with respect to the third dimension (ideally a line). For example, elongated elements may be wires, fibers, threads, yarns, filaments and combinations thereof. In an elongated element one of the three dimensions, i.e. the length, may be, for example, at least ten times greater than the other two dimensions, preferably at least twenty times, more preferably at least fifty times.

According to embodiments, the culture comprising microorganisms is in liquid form, and may be dispensed from the outlet discontinuously, i.e. in some portions of the elongated element only, or continuously, on the entire elongated element, e.g., on the entire yarn. In other words, according to embodiments, the culture may be dispensed from the first outlet discontinuously or continuously.

The culture may be fed to the outlet and the elongated element by a pump. The pump speed is set in order to provide a certain amount of culture to the elongated element.

According to an aspect, when the elongated element (e.g., a yarn) contacts the culture of microorganisms at the outlet, a certain amount of culture is provided to the elongated element. When a certain amount of culture is provided to the elongated element, a certain amount of culture is dispensed from the outlet in order to feed to the elongated element (e.g., a yarn) a fixed amount of culture that provides a sufficient amount of culture to the elongated element, avoiding excessive culture being wasted. In other words, the dispensing of the culture may be substantially continuous, so that the amount of culture at the outlet of the feeding device is kept substantially constant at least during the step of contacting the elongated element with the culture.

For example, the culture comprising microorganisms may be dispensed from the outlet to form a "half-drop" on the elongated element (e.g., a yarn) under the outlet. In this way, advantageously, the culture is dispensed from the outlet of the feeding device at a flow rate selected so that the culture envelops the elongated element, preferably a yarn, but is prevented from falling from the elongated element, and from drying out at the outlet.

In embodiments, the culture of microorganisms is dispensed from said first outlet substantially continuously. In other words, according to embodiments, the culture of microorganisms, e.g. in liquid form, may be dispensed according to a substantially continuous release from at least the first feeding device.

Preferably, the culture of microorganisms is dispensed from said first outlet substantially continuously and the speed of dispensing the culture from the outlet of the feeding device (i.e., the flow rate of the culture dispensed by the outlet of the feeding device) and the speed of supply of the elongated element to the outlet are adjusted so that substantially the entirety of the culture exiting from the outlet is provided to the elongated element (e.g., a yarn) during the step of contacting the elongated element with the culture of microorganisms.

According to embodiments of the present process, the culture of microorganisms is provided to a single elongated element, e.g., a single yarn. In other words, each outlet of a feeding device dispenses, for example, a culture of microorganisms, to a single elongated element, e.g., to a single yarn.

In embodiments, the elongated element provided with the first culture of microorganisms is collected at an elongated element take-up device, such as a yarn take-up device, for example, a take-up bobbin.

In embodiments, the culture comprising microorganisms is dispensed from the at least feeding device to the elongated element according to a direction that is substantially perpendicular to the direction of supplying of the elongated element.

For example, a yarn may be supplied substantially horizontally from a yarn source to a yarn take-up device, and the culture may be dispensed from the outlet of the feeding device to the yarn in substantially vertical direction.

According to embodiments, the elongated element (e.g., a yarn) is fed to said outlet at a distance whereby the culture exiting the outlet contacts both said outlet and said elongated element during said elongated element contacting step. Preferably, the elongated element is supplied to said outlet at a distance whereby the culture exiting the outlet contacts both said outlet and said elongated element (e.g., a yarn), and whereby substantially the entirety of the culture exiting from the outlet is provided to the elongated element during the step of contacting the elongated element with the culture of microorganisms.

In other words, the outlet from which the culture comprising microorganisms is dispensed to the elongated element (e.g., a yarn) and the elongated element are separated by a distance which is selected so that the culture exiting the outlet contacts both the outlet and the elongated element, e.g., a yarn. For example, according to embodiments, a yarn may be positioned close enough to the outlet of the feeder (i.e., the feeding device) so that the culture extends from the outlet (e.g., a nozzle) of the feeder to the yarn (i.e., the elongated element) in a substantially continuous way. In this way, advantageously, the dispensed culture is substantially prevented from falling down or drying out. As above mentioned, the culture may be dispensed to form a "half-drop" on the elongated element under the outlet, during the step of contacting the elongated element with the culture.

As used herein, the term "half-drop" refers to a portion of liquid, e.g., the culture comprising microorganisms in a liquid medium, or the culture medium only, at the outlet of a feeding device, with which the elongated element (e.g., a yarn) is contacted and through which the elongated element is led to receive an amount of culture liquid. In other words; the term "half-drop" refers to the space region occupied by the culture at the outlet of the feeding device at least during the step of contacting the elongated element with the culture coming from the device. The culture of microorganisms, or the culture medium, exiting from an outlet of the feeding device may visually resemble to the shape of a "half-drop", during the step of contacting the elongated element (e.g., a yarn) with the culture liquid.

As visible from the figures; preferably the culture extends around the elongated element (e.g., around a yarn), forming a curved portion on the side of the elongated element opposite to the outlet of the feeding device. This amount of culture liquid is referred to as a "half-drop".

According to embodiments, advantageously, the culture of microorganisms is dispensed from at least a first outlet of a first feeding device to an elongated element (e.g., a yarn), which is supplied at the outlet from an elongated element source; the elongated element contacts the culture and then moves away from the outlet, preferably to be collected at an elongated element take-up device.

Advantageously, the elongated element passing at the outlet is impregnated by the culture exiting from the outlet. In other words; the elongated element (e.g., a yarn) moves relatively to the feeding device, so that substantially the entire, preferably the entire, culture dispensed from the outlet of the feeding device is provided to and retained by the elongated element.

In embodiments, the distance between the outlet from which the culture comprising microorganisms is dispensed and the elongated element is in the range of 0.1 mm to 5 mm, preferably of 0.5 mm to 2 mm.

According to embodiments, substantially the entire amount of the culture dispensed from the outlet is provided to the elongated element.

According to embodiments, the process further comprises a step f) of incubating the elongated element obtained in said step e).

According to embodiments, the elongated element obtained in said step e) (i.e., the elongated element, for example a yarn, provided with an amount of at least a culture of microorganisms) is incubated in air and/or in an incubator.

Advantageously, according to embodiments, the incubator is a device which allows to grow microorganisms under controlled conditions, and may be, for example, a closed device (such as a closed box) which substantially prevent the drying of the microbial culture and also substantially prevent the contamination of the culture on the elongated element.

Suitable incubators are per se known in the art.

According to embodiments, the incubator may integrate one or more elements configured to prolong the residence time of the elongated element in the incubator.

For example, elements configured to prolong the residence time of the elongated element in the incubator may be elements configured to change the direction of the elongated element in the incubator and/or elements configured to partially wind the elongated element inside the incubator.

Preferably, the elements configured to prolong the residence time of the elongated element in the incubator are rotatable elements.

For example, the elements configured to prolong the residence time of the elongated element in the incubator may be one or more pulley and/or one or more bobbin.

According to embodiments, elements configured to prolong the residence time of the elongated element in the incubator may be elements configured to change the direction of the elongated element, i.e. elements configured to deviate the elongated element (e.g., a yarn) which passes through the incubator. For example, when the incubator integrates one or more elements configured to change the direction of a yarn, the path of the yarn inside the incubator may comprise curves and/or serpentines and/or switching of path's level, so that the yarn moves according to a "multi-level" or "tridimensional" path.

According to embodiments, the process further comprises a step of collecting, e.g. at an elongated element take-up device, the elongated element provided with the culture of microorganisms from step e) or f) in a suitable form. In other words, according to embodiments, the process may further comprise a step of collecting the elongated element provided with the culture of microorganisms in a suitable form before and/or after an incubation step.

For example, in embodiments, a yarn provided with the culture of microorganisms may be collected at a yarn take up device, e.g., by winding around a take-up bobbin.

According to embodiments, the collecting of the elongated element provided with the culture of microorganisms may be performed within the incubator.

Advantageously, according to embodiments, the process comprises the step of selectively varying the speed of said dispensing of said first culture as a function of the speed of supply of the elongated element, and/or as a function of the absorption capacity of the elongated element, and/or the dimension of said at least one elongated element.

According to embodiments, the process comprises the step of selectively varying the speed of supply of the elongated element (e.g., a yarn), as a function of the speed of said dispensing of said first culture, and/or as a function of the absorption capacity of the elongated element, and/or the dimension of said at least one elongated element.

According to embodiments, the speed of the supply of the at least one elongated element (for example, a yarn) is in the range of 0.1 m/min to 10 m/min, preferably 0.5 m/min to 5 m/min, more preferably 0.8 m/min to 2 m/min.

According to embodiments, the speed of dispensing of said culture (i.e., the flow rate of the culture dispensed by the feeding device) is in the range of 0.01 ml/min to 0.5 ml/min, preferably of 0.05 ml/min to 0.2 ml/min.

According to embodiments, at least a second outlet is provided, preferably downstream said first outlet.

According to embodiments, the second outlet may be the outlet of a second feeding device or a second outlet of the first feeding device.

According to embodiments, said at least second outlet dispenses a second culture of microorganisms (e.g., in liquid form) or a culture medium.

According to embodiments, the second culture may be the same of the first culture comprising microorganisms. In this way, advantageously, said at least first culture is dispensed by a plurality of outlets to at least one elongated element, such as a yarn.

According to embodiments, a culture medium that is suitable to be added to the first culture comprising microorganisms, may be provided to the elongated element through at least a second outlet.

According to embodiments, at least a first culture comprising at least one microorganisms and/or at least one culture medium is dispensed to the elongated element within said incubator.

According to embodiments, the elongated element obtained in step e) of the process of the invention (i.e., the elongated element provided with an amount of at least a culture of microorganisms) may be collected within an incubator. According to embodiments said culture of microorganisms comprises at least one microorganism selected from bacteria, yeasts, fungi, algae and mixtures thereof.

According to embodiments, the culture of microorganisms comprises at least one microorganism able to provide a microbial-product and/or a microbial precipitate onto the elongated element, e.g., onto a yarn.

As used herein, the terms "culture", "microbial culture", "culture of microorganisms" and "culture comprising at least a microorganism" refer to at least one microorganism in a medium, wherein the medium is suitable for the growth and multiplication of the microorganism. A culture may be a co-culture including two or more different microorganisms.

As used herein, the term "co-culture" refers to at least two different microorganism in a medium, wherein the medium is suitable for the growth and multiplication of all the microorganisms included therein. Said different microorganisms may be substantially simultaneously cultured, optionally onto a support material, e.g., an elongated element such as a yarn. For example, a co-culture may include biopolymer-producing and dye-producing microorganisms. In this case, advantageously, when such co-culture is provided to an elongated element (e.g., a yarn) according to the process of the invention, an elongated element including a dyed biopolymer may be obtained according to a "concurrent" process, wherein the production of the biopolymer and of the dye, occurs during a single step of culturing (e.g., a single incubation). Microorganisms that are suitable to be co-cultured according to the process of the invention are disclosed, for example, in the International application number PCT/EP2019/058800, having title "A PROCESS FOR PREPARING A DYED BIOPOLYMER AND PRODUCTS THEREOF", in the name of the present Applicant.

As used herein, the term "culture in liquid form" refer to a culture comprising at least one microorganism wherein the medium is in liquid form, i.e., is a liquid medium.

In this context, the term "microbial product" refers to any molecule and/or metabolite that can be produced by a microorganism. Exemplary microbial products are biopolymers, enzymes and dyes.

As used herein, the terms "biopolymer" and "microbial polymer" refer to all the polymers the can be produced by a microorganism.

As used herein, the term "microorganism" refers to small unicellular or multicellular living organisms that are too small to be seen with naked eye but are visible under a microscope, and encompasses bacteria, yeast, fungi, viruses and algae. The term "microorganism" encompasses not genetically modified (i.e. wild type) microorganisms and genetically modified microorganism. For example, a microorganism can be genetically modified in order to produce a microbial product and/or a microbial precipitate which is not produced by the same microorganism when it is not genetically modified (i.e., when it is a wild type microorganism).

In this context the term "microbial precipitate" refers to any material the precipitation of which, for example from a culture medium to a substrate, may be performed and/or induced by a microorganism. An exemplary "microbial precipitate" is calcium carbonate, also known as "calcite".

Advantageously, according to embodiments, the step of incubation may be performed within an incubator adapted for providing environmental condition suitable for culturing the microorganisms provided onto the elongated element, in order to obtain the production of a microbial product and/or a microbial precipitate by the microorganism.

Advantageously, the process of the invention allows for the production of an elongated element (e.g., a yarn) that is provided at least in part with a microbial product (e.g., a microbial biopolymer and/or an enzyme and/or a dye) and/or a microbial precipitate (e.g., calcite).

For example, the production of a microbial product and/or a microbial precipitate by the microorganism may be facilitated by providing a suitable environment for keeping the elongated element humid and preventing the drying of the culture during incubation.

According to embodiments, a medium supplement comprising nutrients and optionally wetting agents and/or dispersing agents may be fed to the elongated element into the incubator and/or before the incubation.

According to embodiments, the microbial product is a biopolymer and/or an enzyme and/or a dye.

According to embodiments, the microbial product is a biopolymer selected from a sugar-based biopolymer, preferably microbial cellulose, and an amino acid-based biopolymer, preferably microbial collagen, or a mixture thereof.

According to embodiments, the biopolymer, i.e., the microbial biopolymer is selected from the group consisting of microbial cellulose, microbial collagen, microbial cellulose/chitin copolymer, microbial silk, and mixtures thereof. These biopolymers are known per se in the art.

According to embodiments, the enzyme is urease.

In a preferred embodiment, said microbial precipitation is a calcite precipitate. Without being bound to a specific scientific explanation, it has been observed that the calcite (calcium carbonate) precipitation is catalyzed by the enzyme urease. In particular, it has been observed that once a culture comprising a microorganisms able to produce urease as a microbial product as above defined, is provided onto the elongated element (e.g., a yarn), the urease is released onto the elongated element, so that the precipitation of the calcite from the culture medium onto the elongated element is obtained.

Accordingly, the urease may be defined as a "precipitant", i.e., an agent which induces the precipitation of substance, to provide a "precipitate", in this case, calcite.

Advantageously, by providing a calcite precipitation to, for example, a yarn, an increase in the tensile strength of the yarn and the whitening of the yarn may be obtained.

Therefore, advantageously, a textile article comprising, for example, yarns provided with calcite obtained by microbial precipitation will be strong, easy to weave and resistant to finishing processes. In addition, the textile article will be whiter and easier to dye with respect to the same article without calcite. Moreover, many processes are generally involved to whiten a yarn or a fabric before dyeing; thus, according to embodiments of the invention, by providing an elongated element, e.g., a yarn, with a calcium carbonate precipitate, the usage of harsh whitening processes and chemicals may be advantageously replaced or substantially reduced.

As above, mentioned, according to embodiments, the microbial product may be a dye.

According to embodiments, the dye, namely the dye that is produced by the microorganisms provided to the elongated element, is selected from indigo dye, indigoid dye, pigment dye and mixture thereof.

Preferably, the dye is indigo dye, and it is produced by a microorganism that is able to produce indigo.

As used herein, the term "indigoid" refers to dye molecules that are indigo-derivatives.

As used herein, the term "pigment dye" refers to dye molecules that are not indigo-derivatives.

According to embodiments, the indigoid dye is selected from any indigoid dye, such as, for example, 6,6'-dibromoindigo, 5-bromoindigo, 5,5'-dibromoindigo, 5,7,5',7'-tetrabromoindigo, 4,5,7,4',5'-pentabromoindigo, 4,5,6,4',5',6'-hexabromoindigo, 7,7'-dimethylindigo, 4,5,4',5'-tetrachloroindigo, and mixtures thereof.

The above mentioned indigoid dyes have to be intended as non-limiting examples of indigoid dyes suitable to be used in the present invention.

According to embodiments, the pigment dye is selected from melanin, anthraquinone, xanthomonadin, indigoidine, astaxanthin, canthaxantin, cycloprodigiosin, granadaene, heptyl-prodigiosin, prodigiosin, pyocyanin, rubrolone, scytonemin, staphyloxanthin, tryptanthrin, undecylprodigiosin, violacein, zeaxanthin, ankaflavin, lycopene, monascorubramin, naphtoquinone, riboflavin, rubropunctatin, β-carotene, torularhodin and mixtures thereof.

The above mentioned pigment dyes have to be intended as non-limiting examples of pigment dyes suitable to be used in the present invention.

As above mentioned, the dye is preferably indigo dye.

According to embodiments, the culture comprising at least one microorganisms comprises microorganisms at a concentration of $1 \times 10^8$ CFU/ml to $1 \times 10^9$ CFU/ml, preferably ranging from $4 \times 10^8$ CFU/ml to $6 \times 10^8$ CFU/ml.

According to embodiments, the microorganism able to produce a biopolymer and/or an enzyme and/or a dye may be selected from bacteria, algae, and mixture thereof.

For example, biopolymer-producing bacteria may be selected from *Gluconacetobacter, Aerobacter, Acetobacter, Achromobacter, Agrobacterium, Azotobacter, Salmonella, Alcaligenes, Pseudomonas, Rhizobium, Sarcina* and *Streptoccoccus, Bacillus* genus, genetically modified *Escherichia coli*, and mixtures thereof, and biopolymer-producing algae may be selected from Phaeophyta, Rhodophyta and Chrysophyta, and mixture thereof.

According to embodiments, enzyme-producing microorganisms, preferably urease-producing microorganisms are selected from *Bacillus* genus, *Sporosarcina, Pseudomonas putida, Myxococcus, Arthrobacter, Synechococcus, Desulfovibrio, Proteus, Prochlorococcus, Halomonas* and *Trichoderma*.

According to embodiments, enzyme-producing bacteria are selected from those of *Bacillus* genus.

According to embodiments, urease-producing bacteria are selected from those of *Bacillus* genus, *Sporosarcina, Pseudomonas putida, Myxococcus, Arthrobacter, Synechococcus, Desulfovibrio, Proteus, Prochlorococcus, Halomonas* and urease-producing fungi are selected from those of *Trichoderma* genus.

Advantageously, urease-producing bacteria are suitable to provide the precipitation of calcium carbonate onto the yarn.

According to embodiments, dye-producing microorganism is selected from dye-producing bacteria, dye-producing fungi and mixture thereof. Preferably dye-producing bacteria are selected from *Chromobacterium violaceum, Serratia marcescens, Chriseobacteium* sp., *Staphylococcus aureus, Streptomyces* sp., *Vibrio* sp., *Corynebacterium* genus, genetically modified *Escherichia coli*, and mixtures thereof. Preferably, dye-producing fungi are selected from *Penicillium, Talaromyces, Fusarium, Scytallidium, Trametes, Xanthomonas; Streptomyces, Aspergillus* and mixtures thereof.

The above mentioned dye-producing bacteria and dye-producing fungi have to be intended as non-limiting examples of dye-producing bacteria and dye-producing fungi suitable to be used in the present invention.

For example, indigo-producing genetically modified *Escherichia coli*, i.e. recombinant *E. coli* are known from the U.S. Pat. No. 4,520,103, the U.S. Pat. No. 5,834,297 and from the scientific papers "Optimization of bio-indigo production by recombinant *E. coli* harboring fmo gene", G H. Han et al (2008), Enzyme and Microbial Technology 42: 617-623, and "Identification of indigo-related pigments produced by *Escherichia coli* containing a cloned *Rhodococcus* gene", Hart, S., K. R. Koch, and D. R. Woods, 1992, J. Gen. Microbiol. 138:211-216.

Advantageously, in a further embodiment said elongated element, is preferably a yarn, more preferably a hydrophilic yarn, and even more preferably a cotton yarn.

According to embodiments of the invention, hydrophilic yarns are natural yarns, i.e. yarns that are made of natural fibers. Preferably, natural yarns comprise natural fibers selected from cotton, wool, flax, kenaf, ramie, hemp, linen and mixtures thereof.

According to embodiments of the invention, hydrophilic yarns may be synthetic yarns. For example, synthetic yarns comprise synthetic fibers selected from polyester, rayon, nylon, lycra and mixtures thereof.

Advantageously, hydrophilic elongated elements, e.g., hydrophilic yarns, are impregnated with the culture comprising microorganisms and/or with liquid culture media in a particularly easy and effective manner.

According to embodiments, a wetting agent may be fed to the elongated element, preferably together with said culture of microorganisms, preferably in an amount in the range of 0.05% to 1% by weight of the final culture weight, more preferably of 0.1% to 0.5% by weight of the final culture weight. According to embodiments, one or more wetting agents may be included into the culture comprising microorganisms before dispensing it to the elongated element (e.g., to a yarn).

Suitable wetting agents suitable to be included into a culture comprising microorganisms are known in the art.

Example of suitable wetting agents are Cottoclann® TR CT, Foryl® DLW, Kieralon® Wash Jet B coni, Primasol® NF, Sanwet® M-25, Sanwet® M-30.

According to embodiments, one or more dispersing agents may be included into the culture comprising microorganisms before dispensing it to the yarn.

Dispersing agents suitable to be included into a culture comprising microorganisms are known in the art.

Advantageously, according to embodiments, through the process of the invention, an elongated element (e.g., a yarn) that is at least in part provided with a biopolymer, preferably a sugar-based biopolymer, more preferably microbial cellulose, may be obtained.

Advantageously, according to embodiments, through the process of the invention, an elongated element (e.g., a yarn) that is at least in part provided with a microbial precipitate, preferably calcite, may be obtained.

Advantageously, according to embodiments, through the process of the invention, an elongated element (e.g., a yarn) that is at least in part provided with a dyed biopolymer, such as, for example, indigo dyed microbial cellulose, may be obtained.

The present invention also relates to an elongated element, for example a yarn, as obtainable by the process according to the present invention.

According to embodiments, at least part of the elongated element as obtainable by the process according to the invention, is provided with a microbial product, preferably a biopolymer, more preferably microbial cellulose, and/or a microbial precipitate, preferably calcite.

According to embodiments, the elongated element provided with a biopolymer, preferably microbial cellulose, may be at least in part dyed.

According to embodiments, at least part of the elongated element provided with a biopolymer, preferably microbial cellulose, may be dyed, preferably indigo dyed, according to methods that are, per se, known in the art.

According to embodiments, the elongated element (e.g., a yarn) as obtainable by the process according to the present invention is dry, optionally dyed, and it is provided with a microbial product (e.g., a microbial biopolymer, such as microbial cellulose) and/or a microbial precipitate.

In another aspect, an object of the present invention is a fabric which comprises an elongated element (e.g., a yarn) as obtainable by the process of the invention. Preferably, said elongated element is dry, optionally dyed, and it is provided with a microbial biopolymer and/or a microbial precipitate.

In embodiments, the fabric is a woven fabric, preferably a denim fabric.

Also object of the invention is a garment comprising an elongated element (e.g., a yarn) as obtainable by the process of the invention, and/or a fabric comprising the elongated element of the invention.

A further object of the invention is an apparatus for carrying out the process of the invention, the apparatus comprising at least a first feeding device having at least one first outlet for dispensing at least a first culture comprising at least one microorganism from said outlet, and at least one first elongated element source to supply at least one elongated element to said device, wherein said apparatus is configured so that said at least a first culture comprising at least one microorganism contacts at least part of said elongated element when said culture is dispensed from said first outlet.

In an embodiment, the apparatus further comprises at least one incubator.

According to embodiments, the apparatus comprises at least a second feeding device having at least one second outlet for dispensing a culture of microorganisms or a culture medium. Advantageously, through said second feeding device and said second outlet a second culture comprising microorganisms and/or a culture medium comprising nutrients may be provided to the elongated element.

According to embodiments, the apparatus is provided with at least an elongated element take-up device for collecting the elongated element after it has been provided with the culture of microorganisms.

For example, an elongated element take-up device may be a yarn take-up device, for example a yarn take-up bobbin.

According to embodiments, the incubator may include the first feeding device, and/or the second feeding device, and/or at least one elongated element take-up device.

According to embodiments, a first incubator may be placed between a first feeding device and a second feeding device, and a second incubator may be placed downstream with respect to the second feeding device.

According to an aspect, the elongated element take-up device is configured to collect the elongated element after that it has been provided with at least the first culture comprising microorganisms.

According to embodiments, the elongated element take-up device is configured to collect the elongated element after that it has been provided with a microbial product and/or a microbial precipitate and/or a dye.

In an embodiment, advantageously, the apparatus further comprises a logic control unit configured to regulate the speed of dispensing of at least said first culture from the feeding device (i.e., the flow rate of the culture dispensed by the feeding device) and/or the speed of supplying the elongated element (e.g., a yarn) from the elongated element source.

Preferably, the apparatus comprises at least one sensor for monitoring at least one parameter relevant to the culture at the outlet. For example, the sensor may provide a signal indicative of the amount of culture exiting the outlet of the feeding device.

According to embodiments, in the apparatus, the sensor is selected from the group comprising a laser light sensor, an image processing sensor and a capacitive sensor.

According to embodiments, the logic control unit may be advantageously configured to control (e.g., adjust) the speed of dispensing of at least said first culture from the feeding device and/or the speed of supply of the elongated element from the elongated element source, in function of the signal coming from at least one sensor.

According to embodiments, in the apparatus, said feeding device comprises a pump, preferably a syringe pump.

According to embodiments, the incubator may integrate at least the first feeding device. In this way, at least a first culture comprising microorganisms may be provided to the elongated element inside the incubator.

For example; the incubator may integrate the first feeding device and the second feeding device to provide, respectively, a culture comprising microorganisms and a culture medium comprising nutrients to the elongated element inside the incubator. In other words, a culture comprising microorganisms and a culture medium comprising nutrients may be provided to the elongated element by two different outlets connected to the incubator.

In a further aspect of the invention, a plant is provided comprising a plurality of apparatuses according to the invention.

Further aspects and advantages of the present invention will be discussed more in detail with reference to the enclosed drawings, which schematically illustrate exemplary embodiments of the invention and that are provided by way of illustrative and non-limiting example.

BRIEF DESCRIPTION OF THE DRAWINGS

FIGS. 8 and 9 schematically show a particular embodiment of the invention, in which the incubator integrates the elongated element take-up bobbin and the feeding device for dispensing a culture comprising microorganisms, and/or a culture medium comprising nutrients to the elongated element;

FIG. 10 shows an embodiment of the invention wherein the incubator integrates both the first feeding device and the second feeding device;

FIG. 11 schematically shows an embodiment of the invention, in which the incubator integrates a plurality of elements configured to prolong the residence time of the elongated element in the incubator.

DETAILED DESCRIPTION OF THE INVENTION

The invention will now be described with reference to FIGS. 1 to 11, wherein the present invention will be described with reference to exemplary embodiments wherein a culture comprising microbial cellulose producing microorganisms is provided to an elongated element, in particular to a yarn. In such Figures, reference is made to a yarn as the elongated element; however, as above discussed, different elongated elements may be used. As above discussed, the elongated element may be, for example, a fiber, a filament, a yarn, a thread, a wire and a combination thereof.

Although in the following specific examples are provided, which refer to the use of bacteria for the production of microbial cellulose, it is to be noted that the scope of the present invention encompasses any culture of microorganisms which are able to produce a microbial product and/or a microbial precipitate onto the yarn. The culture of microorganisms may, for example, comprise at least one microorganism selected from bacteria, yeasts, fungi, algae and mixtures thereof. The microbial product produced by the microorganisms may be a biopolymer such as a sugar-based biopolymer, such as microbial cellulose or an amino-acid-based biopolymer, such as microbial collagen, or a mixture thereof.

According to embodiments, the product of the microorganisms may be a precipitate (i.e., a product obtained by precipitation), such as a calcite precipitate. As above discussed, without being bound to a specific scientific explanation, it has been observed that the precipitation of calcite or calcium carbonate, is catalyzed by the enzyme urease, which can be advantageously produced by bacteria, such as bacteria of the *Bacillus* group.

According to an aspect of the invention, any kind of microorganisms may be used, which produce a biopolymer or, as precipitants, cause the precipitation of any other substance which may provide the yarn with advantageous properties.

According to embodiments, the product of the microorganisms may be a dye.

According to embodiments, the dye, namely the dye that is produced by the microorganisms provided to the elongated element, is selected from indigo dye, indigoid dye, pigment dye and mixture thereof.

Figure 1:
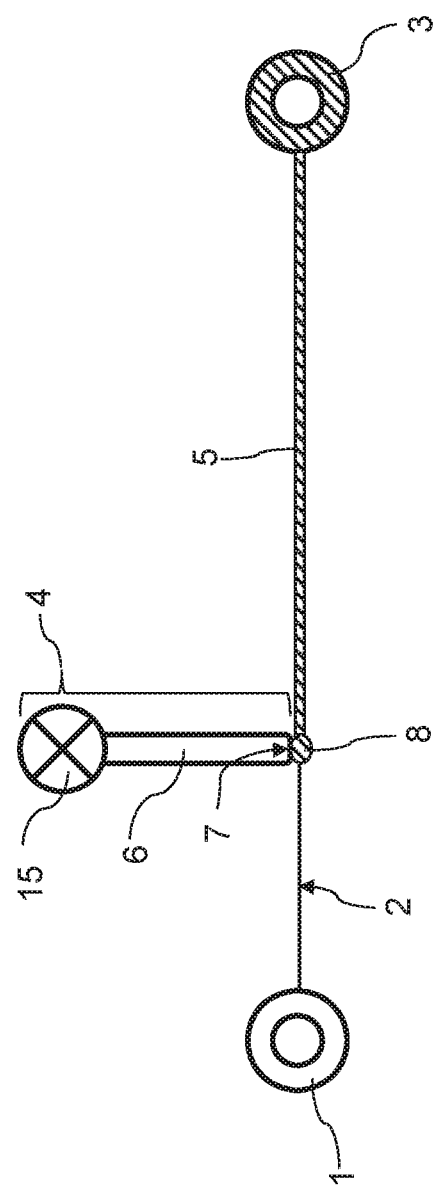
FIG. 1 schematically illustrates an embodiment of the invention wherein an apparatus according to the invention dispensing a culture comprising microorganisms to an elongated element.

As above mentioned, FIG. 1 schematically illustrates an embodiment of the invention wherein an apparatus according to the invention dispensing a culture comprising microorganisms to an elongated element, i.e., to a yarn.

In FIG. 1, reference numeral 1 indicates an elongated element source 1, i.e., a yarn source 1, such as a yarn feeding bobbin, from which an elongated element 2, i.e., a yarn 2 may be substantially continuously supplied in the direction of a elongated element take-up device 3, i.e., a yarn take-up device 3, for example a yarn take-up bobbin, which collect the elongated element (i.e., the yarn) provided with a culture 5 comprising at least a microorganism, at the end of the process. The elongated element 2 may be a hydrophilic yarn, such as a cotton yarn.

The culture 5 comprising microorganisms is provided onto the yarn 2 by first feeding device 4 through a first outlet 7.

First feeding device 4, i.e., a microbial culture feeder, may comprise, for example, a first feeding pipe 6 containing a microbial culture 5, and a pump 15 to provide and regulate the dispensing of the culture 5 from the feeding pipe 6 through the first outlet 7. The first outlet 7 is, according to the embodiment of FIG. 1, positioned at one end of the feeding pipe 6 and may be, for example, a nozzle.

The first feeding device 4 is positioned at a predetermined distance from the elongated element source 1 and are provided with a pump 15, preferably a syringe pump, a feeding pipe 6 and a first outlet 7, from which the culture 5 exits substantially in a perpendicular direction with respect to the supply direction of the yarn 2.

According to the embodiment shown in FIG. 1, the culture 5 comprising microorganisms 5 is dispensed from the first outlet 7 so that the culture contacts both the yarn 2 and the outlet 7 substantially at the same time. Preferably, the feeding device 4 is configured so that the culture 5 is dispensed from the first outlet 7 in an amount that envelops the yarn (i.e., the elongated element) to form a half-drop 8, which contacts both the yarn 2 and the outlet 7 substantially at the same time, preferably at the same time. Advantageously, the feeding device 4 is configured so that the culture 5 is dispensed from the first outlet 7 in a substantially continuous manner, according to a pre-selected amount and/or speed in order to substantially avoid the culture, i.e., the half-drop 8 of culture 5 from dripping from the yarn 2, or from drying out on the outlet 7.

According to embodiments, the first outlet 7 and the yarn 2 may be separated by a distance which is selected so that the culture 5 contacts both the outlet 7 and the yarn 5 when it is dispensed from the feeding device 4, According to embodiments, this distance may range from 0.1 mm to 5 mm, preferably from 0.5 mm to 2 mm. Advantageously, by adjusting the distance between the first outlet 7 and the yarn 2 and/or the speed of supply of the yarn 2 and/or the speed of dispensing the culture 5 (i.e., the flow rate of the culture 5 dispensed by the feeding device 4), advantageously, substantially the entire amount of the dispensed culture 5 may be provided to the yarn 2, preferably substantially continuously.

According to embodiments, the microbial culture 5 may comprise microorganisms at a concentration of $1\times10^8$ CFU/ml to $1\times10^9$ CFU/ml, preferably ranging from $4\times10^8$ CFU/ml to $6\times10^8$ CFU/ml. In this case, advantageously, the concentration of the microorganism allows the production of the biopolymer and/or enzyme and/or precipitate and/or dye onto the elongated element in a short time.

The elongated element source 1, i.e., the yarn source 1 and the elongated element take-up device 3, i.e., the yarn take-up device 3, are positioned with respect to the culture feeder 4 in such a way that the elongated element 2, i.e., the yarn 2, contacts the culture exiting from the outlet 7 by passing through the flow of culture 5, so that and the yarn 2 is impregnated with the microbial culture 5. In this way, advantageously, the yarn 2 picks up a predetermined amount of culture 5. Moreover, the speed of dispensing of the culture 5 and/or the speed of supplying of the yarn 5 may be adjusted so that the yarn 2 is homogeneously impregnated with the microbial culture 5 throughout its length. In other words, the speed of dispensing of the culture 5 and/or the speed of supplying of the yarn 2 may be adjusted so that a predetermined amount of culture 5 provided to the yarn 2 is substantially the same throughout the length of the yarn 2. Preferably, the amount of culture dispensed from the outlet 7 may be adjusted as function of the amount of the amount of culture 5 provided to the yarn 2 passing at the outlet 7, so that substantially the entirety (preferably the entirety) of the culture exiting from the outlet 7 is provided to the elongated element 2, i.e., to the yarn 2, preferably in a substantially continuous manner.

The substantially continuous dispensing of the culture from the outlet 7 to a yarn 2, which may be substantially continuously supplied to the outlet 7, advantageously allows to provide substantially the entirety of the culture exiting from the outlet 7 to the yarn 2, thus effectively preventing the culture from dripping from the yarn 2, and, therefore, effectively preventing the production of culture waste.

According to embodiments, the dispensing speed of the first culture 5 is varied according to the speed at which the elongated element 2 is supplied, and/or according to the absorption capacity of the elongated element 2 and/or the dimension of the elongated element 2. For example, the speed at which an elongated element 2 (i.e., a yarn 2) is supplied by the elongated element source 1 may range from 0.1 m/min to 10 m/min, preferably from 0.5 m/min to 5 m/min and more preferably from 0.8 m/min to 2 m/min.

For example, the speed at which the microbial culture 5 is dispensed from the outlet 7 may range from 0.01 ml/min to 0.5 ml/min, preferably from 0.05 ml/min to 0.2 ml/min.

According to embodiments, the speed at which the elongated element 2 is supplied is varied in function of to the dispensing speed of the first culture 5 (i.e., the flow rate of the culture 5 dispensed from the outlet 7 of the feeding device 4), and/or in function of the absorption capacity of the elongated element 2 (e.g., the yarn 2) and/or the dimension of the elongated element 2 (e.g., the yarn 2).

After having received an amount of culture comprising microorganisms 5, the elongated element moves towards the take-up device 3. The feeding device 4 and the take-up device 3 are separated by a preselected distance, so that the elongated element 2 (e.g., the yarn 2) which has been provided with the microbial culture 5 is exposed to air for a predetermined period, which may range, for example, from 1 to 60 minutes. In this way, the elongated element (i.e., the yarn) is incubated in air, so that the microorganism on the elongated element are grown to produce the required amount of microbial product and/or of microbial precipitate. For example, a yarn 2 may be impregnated with a culture 5 comprising a biopolymer-producing bacteria and incubated in air in order to provide the yarn with a predetermined amount of biopolymer. For example, the biopolymer may be microbial cellulose produced by a bacterium, such as *Acetobacter xylinum*.

In general, the amount of microbial cellulose that can be provided to an elongated element, e.g., a yarn, according to the process of the invention, is in the range from 0.05 to 0.15 g/m (i.e., grams of microbial cellulose for meter of elongated element, e.g., of yarn), preferably in the range from 0.07 to 0.13 g/m).

According to embodiments of the invention, the amount of microbial cellulose is in the range from 0.05 to 0.08 g/m.

According to embodiments of the invention, the amount of microbial cellulose is in the range from 0.08 to 0.15 g/m.

For example, in the following table (Table 1) examples of air incubation periods for different weights of microbial cellulose yield, for the same amount of microbial culture provided to a cotton yarn are listed.

TABLE 1

| Cotton yarn (10/1) weight | Incubation period (min.) | Weight of microbial cellulose (g) |
|---|---|---|
| 100 g | 1 | 0.2 |
| 100 g | 10 | 2 |
| 100 g | 30 | 6 |
| 100 g | 60 | 12 |

According to embodiments, the microbial culture 5 may comprise different microorganisms, i.e., may be a co-culture of microorganisms. For example, the microbial culture may comprise both biopolymer-producing microorganisms and dye-producing microorganisms. In this case the elongated element 2 (e.g., a yarn 2) may be impregnated with the culture 5 comprising both biopolymer-producing microorganisms and dye-producing microorganisms, and then incubated, in air and/or in an incubator, in order to provide the elongated element 2 with a dyed biopolymer.

For sake of simplicity, in the present Figures, reference numeral 5 indicates a microbial culture that has been provided to the elongated element, for example to a yarn. In other words, reference numeral 5 in the present Figures indicates an elongated element (e.g., a yarn) that has been provided at least with a first microbial culture.

Also, for sake of clarity, in present FIGS. 5-11, the incubator is schematically represented as a transparent box, in order to show the elements that are placed inside the incubator in the different represented exemplary embodiments.

The size of the half-drop 8 of microbial culture (i.e., the volume occupied by the culture at the outlet 7) may be measured, according to known methods, and the flow rate of the culture to form the half-drop 8 may be adjusted in order to provide a predetermined quantity of microbial culture 5 at the outlet 7 and to the elongated element 2, for example, when the elongated element is a yarn, according to the yarn diameter, absorption capacity of the yarn and yarn hairiness/fluffiness and/or hydrophilic/hydrophobic properties. In this way, advantageously, it is possible to deposit onto the elongated element 2 substantially the entirety of the culture 5 dispensed from the outlet 7, substantially in a continuous manner, substantially avoiding the culture from falling down from the outlet 7 and/or from the elongated element 2, and being wasted.

The adjustment of the size of the culture half-drop 8 may be performed continuously during the process, for example, according to a negative feedback, or pre-emptively, before each production run, based on previously collected data.

For example, advantageously, the apparatus may further comprise a logic control unit configured to regulate the flow rate of the culture. For example, one or more sensor may provide a signal indicative of the amount of culture exiting the outlet 7 of the feeding device 4, e.g., the size of the half-drop 8 at the outlet 7.

According to embodiments, the logic control unit may be advantageously configured to control (e.g., adjust) the speed of dispensing of at least said first culture from the feeding device 4 and/or the speed of supplying the elongated element 2 (e.g., a yarn 2) from the elongated element source 1, in function of the signal coming from at least one sensor, according to a negative feedback.

Examples of continuous negative feedback loop adjustment systems comprise, in a first embodiment, a laser light passing below the half-drop and forming an optical path between a laser source and a light sensor so that the pump feeding the culture may be slowed down or the elongated element (e.g., yarn) supply speed may be varied in case the drop size exceeds a particular threshold and prevents the laser light from reaching the light sensor.

According to embodiments, additionally or alternatively to the laser, the adjustment may be provided by image processing using a suitable algorithm based on an open source library (e.g. OpenCV library), in order to provide a feedback loop which regulates the size of the half-drop at the outlet.

Additionally or alternatively, according to embodiments, a capacitive sensor is used for measuring the distance between the half-drop 8 and a reference level and thus providing the feedback loop.

Additionally or alternatively, according to embodiments, a possibility to regulate the amount of the culture 5 comprising microorganisms to be dispensed is to dynamically measure the elongated element humidity, e.g., the humidity of a yarn, after impregnation with the culture, and correspondingly adjust the pump speed.

According to embodiments, additionally or alternatively, for example, a calibration of the system before each production run, in order to determine the absorption rate of the elongated element (e.g., the yarn) to be used and accordingly set the pump speed and/or the elongated element speed, and thus the amount of required culture medium for the current run, may be performed. In this case, advantageously, the need of a feedback control may be substantially reduced.

According to embodiments, a wetting agent may be provided to the elongated element. Advantageously, the concentration of the wetting agent may be adjusted, in order to reach the desired injection speed, depending on hydrophilic/hydrophobic properties of the elongated element, which may be pre-determined according to known methods.

According to embodiments, the wetting agent may be added directly to the culture 5 comprising at least one microorganism before its injection onto the elongated element (e.g., a yarn).

Additionally or alternatively, the wetting agent may be fed into the one or more incubators, as discussed in the following. According to embodiments, the wetting agent may be provided within the culture in an amount ranging from 0.05% to 1% by weight of the final culture weight, more preferably ranging from 0.1% to 0.5% by weight of the final culture weight.

Figure 2:
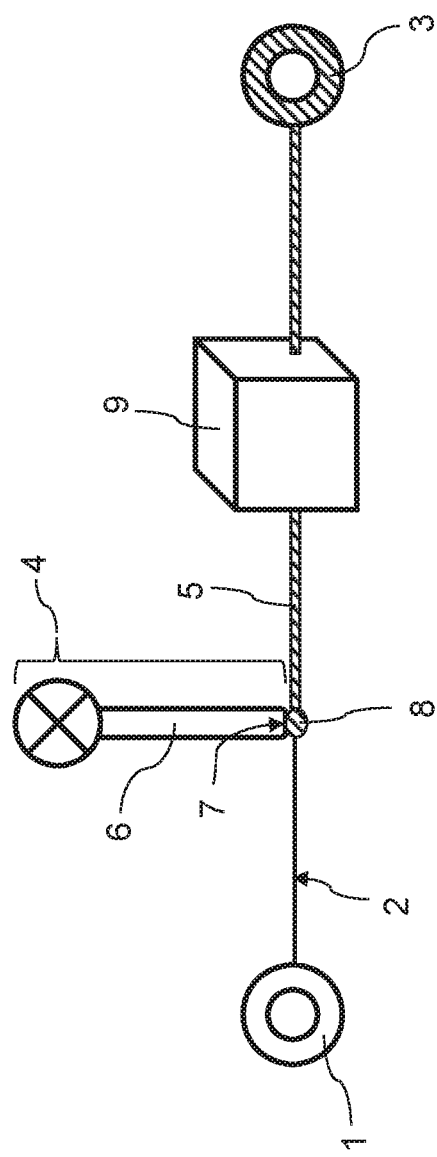
FIG. 2 schematically illustrates an embodiment of the invention wherein an apparatus according to the invention comprises an incubator.

FIG. 2 shows an embodiment of the apparatus according to the invention, wherein an incubator 9 is provided along the elongated element path, downstream with respect to the feeding device 4. The incubator 9 provides, in a way that is known per se, a suitable environment for culturing and growing the microorganisms on the elongated element 2, e.g., a yarn 2. In particular, the incubator provides a suitable environment for keeping the elongated element humid and preventing the drying of the culture during incubation. Moreover, one or more medium supplements, e.g., comprising nutrients and/or wetting agents may be fed into the incubator to further promote the growth of the microorganisms. Also, advantageously, when an incubator is used, the temperature of incubation may be pre-selected and set according to, for example, the microorganism to be grown.

For example, if the microorganism is a microbial cellulose-producing microorganism, during incubation (in air and/or in incubator) microbial cellulose is produced and provided onto the elongated element.

For example, if the microorganism is a urease-producing microorganism, during incubation (in air and/or in incubator) urease is produced and provided onto the elongated element. In this case, advantageously, in the presence of a suitable culture medium, the precipitation of calcium carbonate from the medium onto the elongated element may be obtained.

For sake of simplicity, the present Figures schematically show a yarn (i.e., an exemplary elongated element) moving according to a straight path (for example, inside the incubator). However, according to embodiments, the yarn may take different paths, inside and/or outside the incubator. For example, the path of the yarn may comprise curves and/or serpentines and/or switching of path's level, so that the yarn moves according to a "multilevel" or "tridimensional" path.

Advantageously, by varying the path of the elongated element within the incubator, the residence time of the elongated element in the incubator may be varied, e.g., prolonged.

For example, the longer is the path of the elongated element within the incubator, the longer is the residence time of the elongated element within the incubator, at a predetermined speed of the elongated element.

As above mentioned, according to embodiments, the incubator may integrate one or more elements configured to prolong the residence time of the elongated element in the incubator, such as elements configured to change the direction of the elongated element in the incubator and/or elements configured to partially wind the elongated element (e.g., a yarn) inside the incubator.

Figure 3:
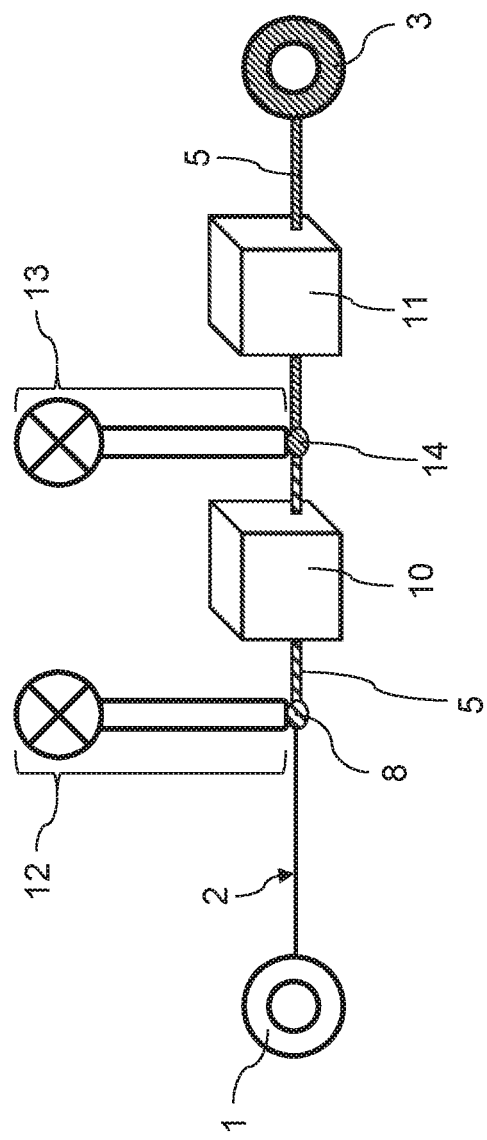
FIG. 3 schematically illustrates an embodiment of the invention wherein an apparatus according to the invention comprises two feeding devices and two incubators.

FIG. 3 shows another embodiment of the apparatus according to the invention, wherein two incubators, i.e., a first incubator 10 and a second incubator 11, and two microbial culture feeding devices, i.e. a first feeding device 12 and a second feeding device 13, are positioned in series, one after the other, along the path of the elongated element. According to the embodiment shown in FIG. 3, the first feeding device 12 dispenses a first culture comprising microorganisms 5 to an elongated element 2 (e.g., to a yarn 2). The elongated element provided with the culture 5 is then incubated for a predetermined time in the first incubator 10. During incubation, the microorganisms are cultured and grown. For example, if the microorganism is a microbial cellulose-producing microorganism, during incubation microbial cellulose is produced onto the elongated element 2. After having exited the first incubator 10, the elongated element 2, already provided with a first amount of culture 5, is contacted with a second "half-drop" 14 of a liquid, dispensed from a second feeding device 13. The second feeding device 13 may dispense again the first culture 5, or a suitable culture medium (i.e., the liquid medium without the microorganisms), or a second culture of microorganisms, different from the first culture dispensed by the first feeding device 12, Subsequently, the elongated element (e.g., a yarn) enters the second incubator 11, where it undergoes a second incubation period. In this way, the amount of microorganisms or culture medium deposited on the elongated element may be increased, in order to fulfil particular needs. For example, if a culture comprising microbial cellulose-producing microorganisms is dispensed both from the first feeding device 12 and the second feeding device 13, microbial cellulose is produced onto the yarn two times, i.e., during a first incubation in the first incubator 10 and during a second incubation in the second incubator 11. Analogously, if a culture comprising microbial cellulose-producing microorganisms is dispensed from the first feeding device 12 and a culture medium is dispensed by the second feeding device 13, microbial cellulose is produced onto the yarn two times, during the two steps of incubation.

For example, if a culture comprising microbial cellulose-producing microorganisms is dispensed from the first feeding device 12 and a culture comprising dye-producing microorganisms (e.g., indigo-producing microorganisms) is dispensed from the second feeding device 13, microbial cellulose is produced onto the elongated element first, i.e., during a first incubation in the first incubator 10, and dye is produced during a second incubation in the second incubator 11. In this way, a dyed biopolymer (e.g., an indigo dyed microbial cellulose) may be obtained, onto the elongated element, according to a two step process.

According to this embodiment of the invention, the process can be defined as a "consecutive" process, wherein the production of the biopolymer and the production of the dye, i.e., the dye molecules, occur substantially sequentially. According to embodiments, biopolymer-producing microorganisms are not removed from the biopolymer before providing dye-producing microorganisms. In this case, advantageously, the thickness of the biopolymer layer increases because the biopolymer-producing microorganisms are still present on the elongated element, when the culture of dye-producing microorganisms is provided.

Additionally or alternatively, according to embodiments, a culture medium comprising nutrients may be injected onto the elongated element or directly on the elongated element feeding bobbin. According to embodiments, other feeding devices and/or outlets (e.g., nozzles) may be additionally placed along the path of the elongated element to supply nutrients in order to further promote the growth of the microorganisms and, for example, the production of a biopolymer onto the elongated element, e.g., to provide a thick layer of biopolymer (such as, microbial cellulose) to the elongated element (e.g., a yarn).

Figure 4:
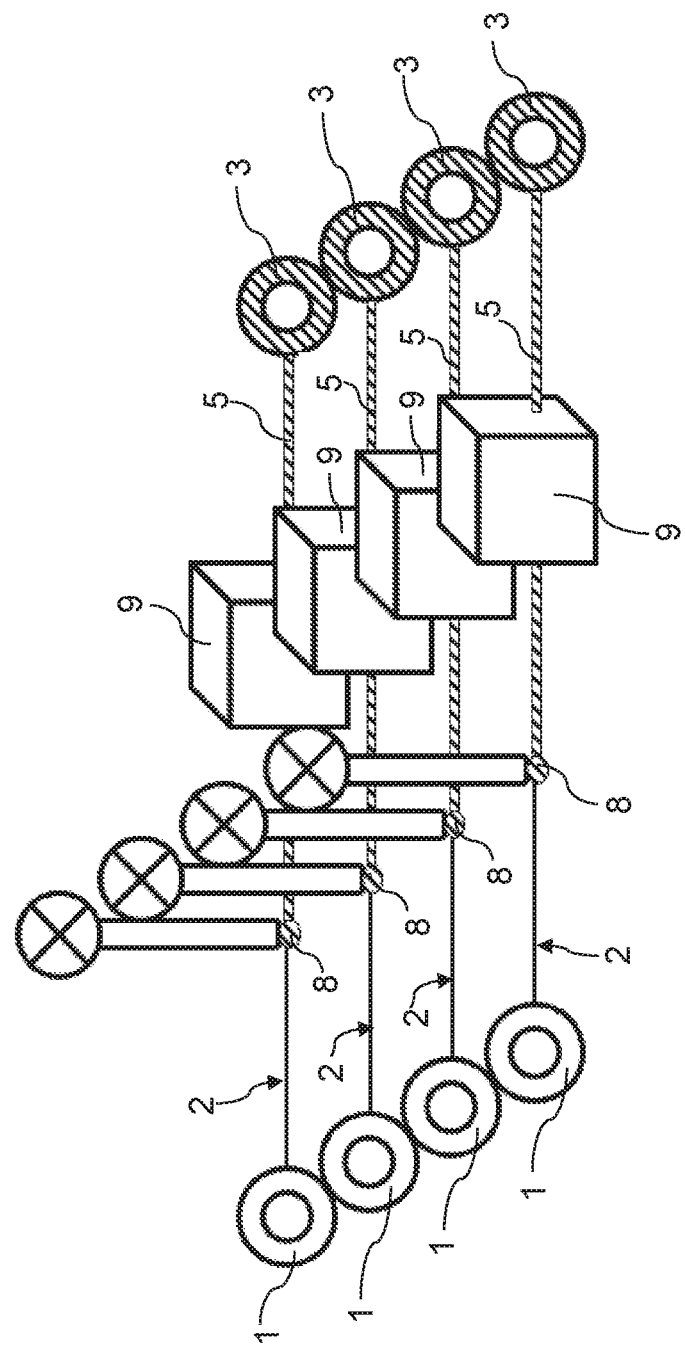
FIG. 4 schematically illustrates an embodiment of the plant according to the invention comprising four apparatuses according to the invention, which are positioned in parallel to each other.

FIG. 4 schematically shows an embodiment of the plant of the invention. In particular, FIG. 4 shows a schematic arrangement of four apparatuses according to the present invention. For sake of simplicity, FIG. 4 shows four apparatuses according to the embodiment discussed with reference to FIG. 2, wherein the four apparatuses are arranged in parallel. When a plurality of apparatuses according to the invention are used, advantageously, a plurality of elongated elements, e.g., yarns, may be provided with one or more cultures of microorganisms substantially at the same time. The different feeding devices may dispense the same or different cultures. The elongated elements 2 may be the same, or may be different elongated elements. The elongated elements 2 may have the same or different features, and may be incubated in the same conditions or in different condition in the different incubators 9. When a plurality of apparatuses according to the invention are used, advantageously, a plurality of elongated elements 2 (e.g., yarns 2) may be provided with different features substantially at the same time. For example, a first yarn 2 may be provided with a predetermined amount of microbial cellulose. A second yarn 2 may be provided with a greater or a lower amount of microbial cellulose with respect to the first yarn. A third yarn 2 may be provided with a predetermined amount of calcite precipitate, and a fourth yarn 2 may be provided with a greater or lower amount of calcite precipitate with respect to the third yarn 2. All other aspects of the apparatus discussed with reference to schematic FIG. 2 apply mutatis mutandis to each of the four apparatuses of the plant schematically represented in FIG. 4.

According to the embodiment of FIG. 4, in each apparatus according to the invention provides a culture of microorganisms to a single elongated element 2, e.g., a single yarn 2. In other words, the outlet of the feeding device of each apparatus according to the invention dispenses, for example, a culture of microorganisms, to a single elongated element 2, e.g., to a single yarn 2.

Figure 5:
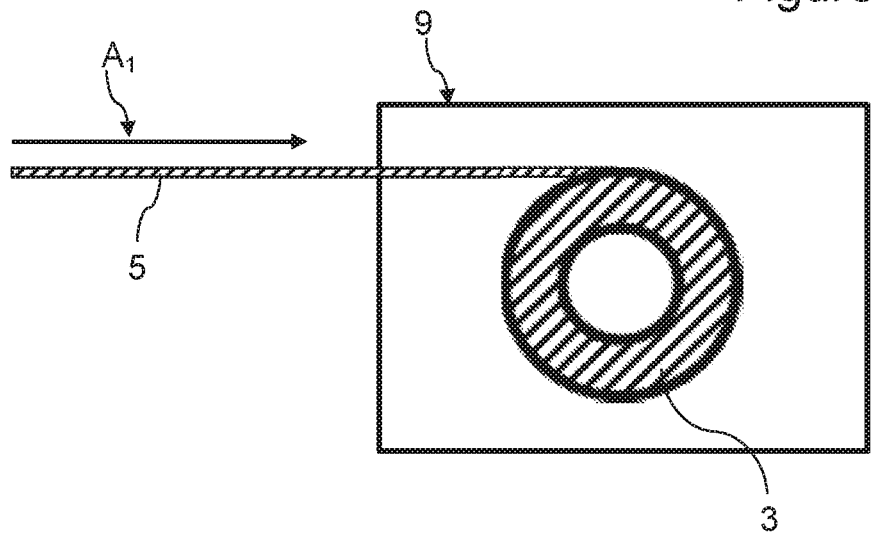
FIGS. 5 and 6 schematically show a particular embodiment of the invention, in which the incubator integrates an elongated element take-up device.
Figure 6:
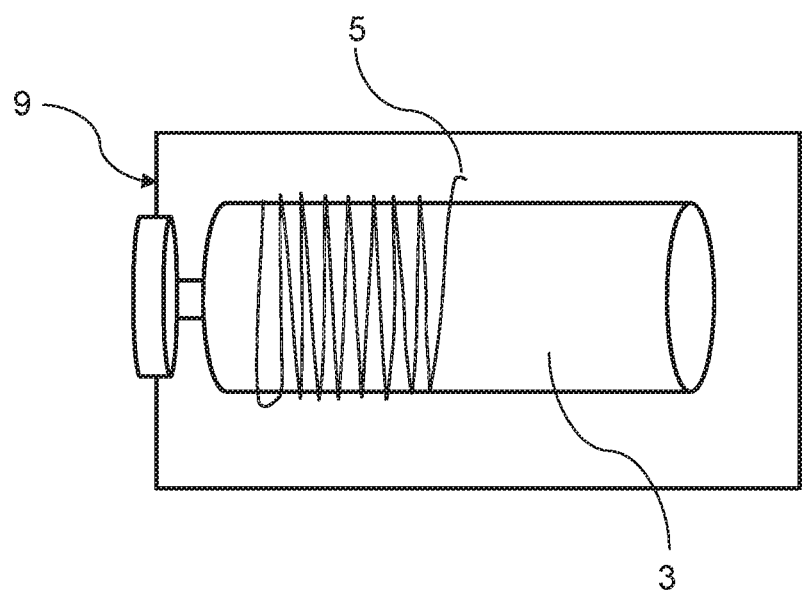

FIGS. 5 and 6 schematically show an incubator according to a particular embodiment of the apparatus of the invention, in which an elongated element take-up device 3 (e.g., a yarn take-up device 3) is integrated within the incubator 9.

Particularly, FIG. 5 is a lateral view of an incubator 9, while FIG. 6 is a frontal view of the incubator 9. The incubator in FIG. 6, with respect to FIG. 5, is observed from a point of view according to arrow $A_1$.

Also, arrow $A_1$ schematically represents the direction according to which the elongated element (e.g., a yarn) provided with a culture 5, comprising at least one microorganism, is supplied to the incubator 9.

According to the embodiment illustrated in FIGS. 5 and 6, the incubator 9 is provided with an elongated element take-up device 3 (e.g., a yarn take-up device 3), for example a bobbin, for collecting the elongated element after that it has been provided with a culture 5 comprising microorganisms. The incubator 9 provides for suitable environmental condition such as, for example, temperature and humidity, for the growing of the microorganisms in the culture 5 onto the elongated element and, according to embodiments, the production of microbial products and/or microbial precipitates and/or dyes, such as biopolymers (for example microbial cellulose), calcite, or indigo.

Figure 7:
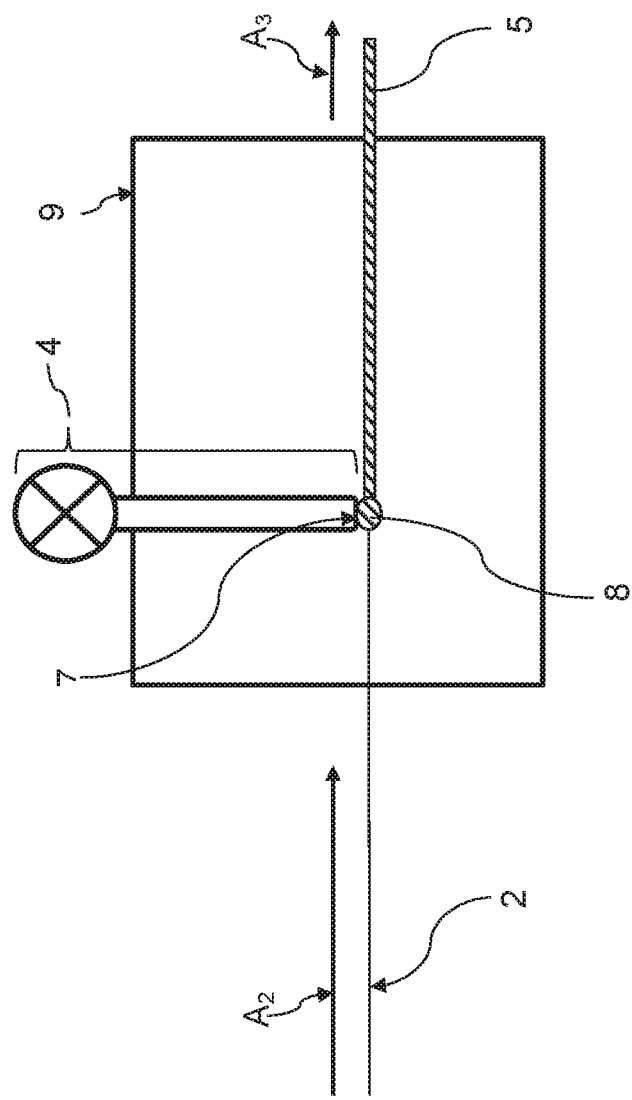
FIG. 7 schematically shows a particular embodiment of the invention, which integrates a first feeding device.

FIG. 7 schematically show an incubator 9 according to a particular embodiment of the invention, which integrates a first feeding device 4.

According to FIG. 7, arrow $A_2$ schematically represents the direction according to which the elongated element 2 (e.g., a yarn 2) is supplied, for example from an elongated element source, to a first feeding device 4, which is integrated in the incubator 9.

According to the embodiment shown in FIG. 7, the culture 5 comprising microorganisms is dispensed from the first outlet 7 so that the culture contacts both the elongated element 2 (i.e., the yarn 2) and the outlet 7 substantially at the same time. Feeding device 4 is configured to dispense a first culture 5 comprising at least one microorganisms from the first outlet 7, as previously disclosed. Culture liquid 5 contacts the elongated element 2, so that the culture 5 is provided to the elongated element 2. After the elongated element 2 has been provided with a predetermined amount of microbial culture 5, it moves outside the incubator 9. According to FIG. 7, arrow $A_3$ schematically represents the direction according to which the elongated element exits from the incubator 9.

According to embodiments, after that the elongated elements exits the incubator 9, it may be further provided with a second culture comprising microorganism and/or with a culture medium.

According to embodiments, after that the elongated elements exits the incubator 9, it may be collected with an elongated element take-up device, such as a yarn take-up bobbin.

FIGS. 8 and 9 show an embodiment of the apparatus of the invention, in which a particular form of the one or more incubators that may be used is shown.

Particularly, FIG. 8 is a lateral view of an incubator 9, while FIG. 9 is a frontal view of the incubator 9. The incubator in FIG. 9, with respect to FIG. 8, is observed from a point of view according to arrow $A_4$.

Also, arrow $A_4$ schematically represents the direction according to which the elongated element 2 (e.g., a yarn 2) enters into the incubator 9, wherein the elongated element 2 is contacted with a culture 5 comprising at least one microorganism, which is supplied by a first feeding device 4, through a first outlet 7, to the elongated element 2.

In the embodiment schematically represented in FIGS. 8 and 9 of the apparatus of the invention, the incubator 9 is provided with an elongated element take-up device 3, (for example, a bobbin may be selected as a particular device for collecting the elongated element, for example a yarn), and with a first feeding device 4. In this case, the first feeding device 4 and the elongated element take-up device 3 are integrated in the incubator 9.

According to the embodiment of FIGS. 8 and 9, a yarn 2 is supplied, for example by a yarn source, and enters into the incubator 9. Inside the incubator 9, a culture 5 comprising microorganisms is dispensed to the yarn 2 from the first outlet 7 of the first feeding device 4. After the yarn 2 has been provided with a predetermined amount of microbial culture 5, it is collected by a yarn take-up device 3, inside the incubator 9.

As above mentioned, in the exemplary embodiment illustrated in FIGS. 8 and 9, a first feeding device 4 is shown, which provides a first culture 5 comprising microorganisms to an elongated element 2, i.e., to a yarn 2.

According to embodiments, in addition to the shown first feeding device 4, at least a second feeding device for the feeding of a second microbial culture and/or a culture medium comprising nutrients may be integrated into the incubator 9.

According to advantageous embodiments, the present invention allows for the production of an elongated element, e.g., a yarn, which may be provided at least in part with a microbial product (for example, a biopolymer, such as microbial cellulose) and/or a microbial precipitate, such as calcite. Such elongated elements, e.g., yarns, may be advantageously used for the production of fabrics and garments.

Also, advantageously, a yarn which has been provided with a biopolymer, e.g., microbial, cellulose may be dyed, e.g., indigo dyed. Dyeing of elongated elements (e.g., yarns) provided with, for example, microbial cellulose, may be performed according to techniques that are, per se, known in the art.

FIG. 10 shows an embodiment of the invention wherein the incubator 9 integrates both a first feeding device 12 and a second feeding device 13.

In the embodiment of FIG. 10, a first feeding device 12 and a second feeding device 13, are positioned in series, one after the other, along the elongated element path, and are both integrated into the incubator 9, so that at least a first culture 5 comprising microorganisms is dispensed to the elongated element 2 inside the incubator 9.

In FIG. 10, the arrow $A_5$ schematically represents the direction according to which the elongated element 2 (e.g., a yarn 2) is supplied, for example from an elongated element source, to the incubator 9. The incubator comprises a first feeding device 12 and a second feeding device 13. The culture 5 comprising microorganisms is dispensed from the first outlet 12, through its first outlet 16, to the yarn 2. The first feeding device 12 dispenses a first culture 5 comprising at least one microorganism to the yarn 2.

Subsequently, the yarn 2, provided with a first amount of culture 5, is contacted with a second culture liquid 14, dispensed from a second feeding device 13, through a second outlet 17. For example, the second feeding device 13 may supply again the first culture 5, or a suitable culture medium comprising nutrients for the microorganisms already provided to the yarn 2 (i.e., the liquid medium without the microorganisms), or a second culture of microorganisms, different from the first culture dispensed by the first feeding device 12. Subsequently, the yarn exits from the incubator 9, according to a direction schematically represented by the arrow $A_6$.

FIG. 11 schematically shows an incubator 9, which integrates a plurality of elements 18 configured to prolong the residence time of the elongated element in the incubator 9.

According to the embodiment of FIG. 11, an elongated element (e.g., a yarn) that has been provided with a culture 5 of microorganisms enters into an incubator 9.

FIG. 11 schematically shows a lateral view of the incubator 9.

Inside the incubator 9, a plurality of elements 18 configured to prolong the residence time of the elongated element in the incubator 9 are present.

In particular, elements 18 are elements that are configured to change the direction of the elongated element, i.e., configured to deviate the elongated element (i.e., the yarn), in the incubator 9.

For example, elements 18 configured to prolong the residence time of the elongated element in the incubator 9 may be pulleys and/or bobbins, and may be preferably rotatable elements.

FIG. 11 shows an embodiment wherein the elements 18 configured to prolong the residence time of the elongated element inside the incubator 9 deviate the elongated element according to a path which substantially define a serpentine.

The incubator 9 includes twelve elements 18 configured to prolong the residence time of the elongated element in the incubator, which are distributed in two series, a first (e.g., upper) series comprising six elements 18, and a second (e.g., lower) series, comprising six elements 18.

According to the embodiment illustrated in FIG. 11, a yarn that has been provided with a culture 5 of microorganisms enters into an incubator 9, and contacts a first element 18 in the first (e.g., upper) series. The yarn is deviated to a second element 18, in the second (e.g., lower) series. The yarn contacts the second element 18 and is deviated to contact a third element 18 in the first series of elements, and subsequently to another element 18 in the second series and again to another element 18 in the first series, and so on until the last element 18. In other words, according to the embodiment illustrated in FIG. 11, the yarn (i.e., the elongated element) sequentially contacts a plurality of elements 18, preferably all the elements 18, alternating one element 18 of the first (e.g., upper) series to an element 18 of the second (e.g., lower) series.

After contacting the last element 18, the yarn exits from the incubator 9.

According to embodiments, elements 18 may be configured to partially wind the elongated element inside the incubator. For example, the elongated element may be wound around a first element 18 one or more times before contacting a second element 18. In this case, the residence time of the elongated element in the incubator in further prolonged.

According to embodiments, the elongated element which exits from the incubator is provided at least in part with an amount of a microbial biopolymer (e.g., microbial cellulose) and/or an amount of a microbial precipitation (e.g., calcite precipitation). Advantageously, the elongated element (e.g., a yarn) which exits from the incubator is provided with an amount of a microbial biopolymer and can be dyed, for example, through common dyed processes.

EXAMPLES

In the following examples, yarn samples was used as elongated element to carry out the process of the invention.

Example 1

A first experiment was carried out using the process and apparatus according to the invention, in which a microbial (bacterial) culture was injected onto yarn samples and the final dry yarn weight was measured in order to determine the amount of microbial (bacterial) cellulose deposited on the yarn. The experiment involved the following steps: About 25 g of yarn were provided on a suitable bobbin. 1200 ml of bacterial culture (BC) of *Gluconacetobacter* were incubated for 2 days at 200 rpm and 28° C. The bacterial cellulose culture was filtered by using a scrim in order to remove cellulosic fibers (produced during the incubation period). 1200 ml of culture were centrifuged at 5000 rpm for 15 minutes and concentrated in order to form a culture having a high concentration of $5.4 \times 10^8$ CFU/ml. 0.5 wt.-% of wetting agent were added to the culture. By using a syringe pump the concentrated culture was injected onto yarn samples (pump speed: 0.1 ml/min, unwinding speed of yarn source bobbin was fixed by voltage used (1.3V)). The yarn provided with the culture *Gluconacetobacter* was incubated for about 10 minutes in air on a 5-meter-long bench. Thereafter, the yarns coated with the bacterial culture were washed with 0.1 M NaOH solution at 80° C. for 20 minutes and neutralized in distilled water. The weight of the yarns, after being dried at room temperature, was measured and the amount of bacterial cellulose deposited on the yarn was determined as being equal to 8.12% with respect to the initial weight of the yarn.

In general, according to embodiments of the invention, the amount of microbial cellulose added may be in the range of 0.05 to 0.08 g/m.

Advantageously, the dried yarn provided with microbial cellulose may be dyed, e.g., indigo dyed, and used in the production of fabrics and/or garments.

Example 2

In a second experiment that was carried out, a bacterial culture was prepared and applied to a yarn as disclosed in the previous Example 1. After the bacterial culture injection onto the yarn, the yarn was wound around a yarn take-up bobbin, which was placed inside an incubator. The yarn provided with the injected bacterial culture was incubated in the incubator. Nutrients were supplied to the yarn inside the incubator by a feeding device. The amount of bacterial cellulose deposited onto the yarn was determined as being equal to 13% with respect to the initial weight of the yarn.

According to embodiments, the amount of microbial cellulose provided may be in the range from 0.08 to 0.15 g/m.

As above mentioned, the dried yarn provided with microbial cellulose may be dyed, e.g., indigo dyed, and used in the production of fabrics and/or garments.

Example 3

A third example of a process according to the invention involves the use of microbially induced calcium carbonate ($CaCO_3$) precipitation (MICP) by a culture of *Bacillus* sp. cells in an urea-$CaCl_2$) medium containing 3 g/L of nutrient broth (Difco), 10 g/L $NH_4Cl$, and 2.12 g/L of $NaHCO_3$ (equivalent to 25.2 mM adjusted to pH 6.0 with 6 N HCl).

Methods and condition of supplying and culturing disclosed in above Examples 1 and 2 apply mutatis mutandis to Example 3.

By providing a yarn with a microbial precipitate, in particular calcite precipitate, advantageously, it is possible to increase the tensile strength of the yarn. Another advantageous effect of microbial calcite precipitation is that calcite provides for a whitening of the yarn. In this way, a yarn which can be easily dyed may be obtained.

Also, the present invention advantageously provides for an environmentally friendly way of processing yarns with respect of conventional processes, substances which may pollute the environment are used.

The dried yarn obtained may be used in the production of fabrics and/or garment.

The present invention provides a novel process for providing, in a substantially continuous, homogeneous, reproducible, contamination-free way, an elongated element, for example a yarn, such as a cotton yarn, with a culture of microorganisms, which preferably produce biopolymers such as microbial cellulose and/or microbial precipitates such as calcite precipitate, and/or dyes such as indigo, which may be provided to at least part of the elongated element to provide the elongated element with advantageous characteristics, as above discussed. The process of the invention allows for the production of, for example, yarns that are suitable to be used in the textile field, in particular in the manufacture of fabrics and garments. The invention is not limited to the embodiments disclosed in the previous description, which are only illustrative and non-limiting, but may be subject to modifications and variants, as envisaged by the skilled in the art, within the protection scope, which is defined by the appended claims.

The invention claimed is:

1. A process for depositing at least a culture (5) of microorganisms to an elongated element (2), comprising the steps of:
   a) providing at least a first feeding device (4) comprising at least a first outlet (7);
   b) supplying at least one elongated element (2), selected from a wire, a fiber, a thread, a yarn, a filament and combinations thereof to said at least first feeding device (4);
   c) feeding to said first outlet (7) at least a first culture (5) comprising at least one microorganism;
   d) dispensing said first culture (5) from said at least first outlet (7);
   e) contacting at least part of said elongated element (2) with said first culture (5) of microorganisms, to provide at least a part of said elongated element (2) with an amount of said first culture (5) of microorganisms;
   said process comprising the step of selectively varying the speed of said dispensing of said first culture (5) in function of the speed of supply of said elongated element (2), and/or as function of the absorption capacity, and/or the dimension of said at least one elongated element (2).

2. The process according to claim 1, wherein said first culture (5) of microorganisms is in liquid form and is dispensed from said first outlet (7) to said elongated element (2) discontinuously or continuously.

3. The process according to claim 1, wherein said elongated element (2) provided with said first culture (5) of microorganisms is collected at an elongated element take-up device (3).

4. The process according to claim 1, wherein said first culture (5) is dispensed to said elongated element (2) according to a direction that is substantially perpendicular to the direction of supply of said elongated element (2).

5. The process according to claim 1, wherein said elongated element (2) is fed to said outlet (7) at a distance whereby said culture (5) exiting said outlet (7) contacts both said outlet (7) and said elongated element (2) during said elongated element contacting step.

6. The process according to claim 5, wherein said distance is in the range of 0.1 mm to 5 mm.

7. The process according to claim 1, further comprising a step f) of incubating the elongated element obtained in said step e).

8. The process according to claim 7, wherein the elongated element obtained in said step e) is incubated in air and/or in an incubator (9).

9. The process according to claim 1, wherein at least a second outlet (17) is provided to dispense a second culture of microorganisms in liquid form or a culture medium.

10. The process according to claim 1, wherein at least said first culture (5) and/or culture medium is dispensed to said elongated element (2) within said incubator (9).

11. The process according to claim 1, wherein said culture (5) of microorganisms comprises at least one microorganism selected from bacteria, yeasts, fungi, algae and mixtures thereof.

12. The process according to claim 1, wherein said culture (5) of microorganisms comprises at least one microorganism able to provide a microbial product and/or a microbial precipitate onto the elongated element (2).

13. The process according to claim 12, wherein said microbial product is a biopolymer and/or an enzyme, and/or a dye, wherein said microbial product is selected from a sugar-based biopolymer, an amino acid-based biopolymer, and urease and wherein said dye is selected from indigo dye, indigoid dye, pigment dye and mixture thereof.

14. The process according to claim 12, wherein said microbial precipitate is calcite precipitate.

15. The process according to claim 1, wherein said culture comprises microorganisms at a concentration $1 \times 10^8$ CFU/ml to $1 \times 10^9$ CFU/ml.

16. The process according to claim 1, wherein said elongated element (2) is a yarn (2).

17. The process according to claim 1, wherein a wetting agent is fed to said elongated element, in an amount in the range of 0.05% to 1% by weight of the final culture weight.

18. An elongated element obtainable by the process of claim 1, wherein at least part of said elongated element is provided with a microbial product, and/or a microbial precipitate.

19. The elongated element according to claim 18, wherein said elongated element is dry and optionally dyed.

20. An apparatus for carrying out the process according to claim 1 comprising at least a first feeding device (4) having at least one first outlet (7) for dispensing at least a first culture (5) comprising at least one microorganism from said outlet (7), and at least one first elongated element source (1) to supply at least one elongated element (2) to said device, wherein said apparatus is configured so that said at least a first culture (5) comprising at least one microorganism contacts at least part of said elongated element (2) when said culture is dispensed from said first outlet (7).

21. The apparatus according to claim 20, further comprising at least one incubator (9).

22. The apparatus according to claim 20, further comprising at least a second feeding device (13) having at least one second outlet for dispensing a culture of microorganisms or a culture medium.

23. The apparatus according to claim 21, wherein said at least one incubator (9) includes said first feeding device (4), and/or said second feeding device (13), and/or at least one elongated element take-up device (3), wherein said elongated element take-up device (3) is configured to collect said elongated element after it has been provided with said culture (5).

24. The apparatus according to claim 20, further comprising a logic control unit configured to regulate the speed of dispensing of at least said first culture and/or the speed of supplying of said elongated element, and further comprising one or more sensors for monitoring culture at the outlet.

25. The apparatus according to claim 20, wherein said feeding device (4) comprise a pump (15).

* * * * *